US006479234B1

(12) United States Patent
Sidransky

(10) Patent No.: US 6,479,234 B1
(45) Date of Patent: *Nov. 12, 2002

(54) DETECTION OF HYPERMUTABLE NUCLEIC ACID SEQUENCE IN TISSUE AND BODY FLUIDS

(75) Inventor: David Sidransky, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/164,764

(22) Filed: Oct. 1, 1998

Related U.S. Application Data

(63) Continuation of application No. 08/854,727, filed on May 12, 1997, now Pat. No. 5,935,787, which is a continuation of application No. 08/299,477, filed on Aug. 31, 1994, now abandoned.

(51) Int. Cl.[7] .......................... C12Q 1/68; C12P 19/34; C07H 21/04
(52) U.S. Cl. .......................... 435/6; 435/91.2; 536/23.1
(58) Field of Search .................... 435/6, 91.2; 536/23.1

(56) References Cited

U.S. PATENT DOCUMENTS

| 4,800,159 A | 1/1989 | Mullis et al. ............ 435/172.3 |
| 5,075,217 A | 12/1991 | Weber ............................. 435/6 |
| 5,380,645 A | 1/1995 | Vogelstein ..................... 435/6 |
| 5,492,808 A | 2/1996 | De La Chapelle et al. ..... 435/6 |
| 5,578,450 A | 11/1996 | Thibodeau et al. ............ 435/6 |
| 5,871,925 A | * 2/1999 | De La Chapelle ............. 435/6 |

FOREIGN PATENT DOCUMENTS

| WO | 9419492 | 2/1994 |
| WO | WO 9419492 | 9/1994 |

OTHER PUBLICATIONS

Brugieres et al., Cancer Research, Feb. 1993, vol. 53, pp 452–455.*
Gonzalez–Zulueta, et al, "Microsatellite Instability in Bladder Cancer" Cancer Research, 53, 5620–5623, Dec. 1993.*
Merlo et al., "Frequent Microsatellite Instability in Primary Small Cell Lung Cancer" Cancer Research, 54, 2098–2101, Apr. 15, 1994.*
Ah–See et al "An Allelotype of Squamous Carcinoma of the Head and Neck Using Microsatellite Markers" Cancer Research 54, 1617–1623, Apr. 1, 1994.*
King, et al., A Polymerase Chain Reaction–Based Microsatellite Typing Assay Used for Tumor Cell Line Identification, American Journal of Pathology, vol. 144, No. 3, Mar. 1994, pp. 486–491.

Wang et al., Brief Report: Polymorphic Microsatellite Markers for the Diagnosis of Graft–Versus–Host Disease, The New England Journal of Medicine, Feb. 10, 1994, vol. 330, No. 6, pp. 398–401.
Noble et al. A Rapid PCR–Based Method to Distinguish Between Fetal and Maternal Cells in Chorionic Biopsies Using Microsatellite Polymorphisms, Disease Markers, vol. 9, pp. 301–306, 1991.
Strand, et al. Destablilization fo tracts of simple repetive DNA in yeast by mutations affecting DNA mismatch repair, Nature, vol. 365, pp. 274–276, Sep.16, 1993.
Ionov et al. Ubiquitous somatic mutations in simple repeated sequences reveal a new mechanism for colonic carcinogenesis, Nature, vol. 363, pp. 558–561, Jun. 10, 1993.
Palombo et al. Mismatch repair and cancer, Nature vol. 367, pp. 417, Feb. 3,1994.
Thibodeau et al., Science, vol. 260, May 7, 1993, pp. 816–819.
Hayashi et al. Cancer Research, vol. 54, 3853–3856, Jul. 15, 1994.
Sidransky et al. Science, vol. 252, May 3, 1991, pp. 706–709.
Sidransky et al., Science, vol. 256, Apr. 3, 1992, pp. 102–105.
Peltomaki et al. Cancer Research, vol. 53, Dec. 15, 1993, pp. 5853–5855.
Hayashi et al., Genetic Diagnosis Identifies Occult Lymph Node Metastases Undetectable by the Histopathological Method, Cancer Research 54, pp. 3843–3856, Jul. 15, 1994.
Peltomaki et al. Microsatellite Instability is Associated with Tumors that Characterize the Hereditary Non–Polyposis Colorectal Carinoma Syndrome, Cancer Research, 53, pp. 5853–5855, Dec. 15, 1993.
Peltomaki et al. Genetic Mapping of a Locus Predisposing to Human Colorectal Cancer, Science, vol. 260, May 7, 1993, pp. 810–819.
Hayashi et al., "Genetic Diagnosis Identifies Occult Lymph Node Metastases Undectable by the Histopathological Method," Cancer Research, 54, 3853–3856.
Ionov et al., "Ubiquitous somatic mutations in simple repeated sequences reveal a new mechanism for colonic carcinogenesis." Nature, vol. 363, 558–561.

* cited by examiner

*Primary Examiner*—W. Gary Jones
*Assistant Examiner*—Jehanne Souaya
(74) *Attorney, Agent, or Firm*—Banner & Witcoff, Ltd.

(57) ABSTRACT

An assay for detection of a mammalian cell proliferative disorder associated with a hypermutable nucleic acid sequences is provided. The identification of particular hypermutable sequences such as microsatellite loci correlates with a particular cancer, thereby allowing detection of both primary tumors and metastatic sites within a patient.

17 Claims, 2 Drawing Sheets

N  T  20%  10%  5%  1%  .5%  .1%

N  T  20%  10%  5%  1%  .5%  .1%

B27

N  T  U

SEQUENCE LISTING (1) GENERAL INFORMATION:

(iii) NUMBER OF SEQUENCES: 40

(2) INFORMATION FOR SEQ ID NO: 1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 1:

CTTGTGTCCC GGCGTCTG                                                    18

(2) INFORMATION FOR SEQ ID NO: 2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 2:

CAGCCCAGCA GGACCAGTA                                                   19

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 3:

TGGTAACAGT GGAATACTGA C                                                21

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 4:

ACTGATGCAA AAATCCTCAA C                                                21

(2) INFORMATION FOR SEQ ID NO: 5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 5:

GATGGGCAAA CTGCAGGCCT GGGAAG                                           26

(2) INFORMATION FOR SEQ ID NO: 6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 6:

GCTACAAGGA CCCTTCGAGC CCCGTTC                                          27

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 7:

GATGGTGATG TGTTGAGACT GGTG                                                    24

(2) INFORMATION FOR SEQ ID NO: 8:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 8:

GAGCATTTCC CCACCCACTG GAGG                                                    24

(2) INFORMATION FOR SEQ ID NO: 9:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 9:

GTTCTGGATC ACTTCGCGGA                                                         20

(2) INFORMATION FOR SEQ ID NO: 10:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 10:

TGAGGATGGT TCTCCCCAAG                                                         20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 11:

AGTGGTGAAT TAGGGGTGTT                                  20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 12:

CTGCCATCTT GTGGAATCAT                                  20

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 13:

CTGTGAGTTC AAAACCTATG G                                21

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 14:

GTGTCAGAGG ATCTGAGAAG                                                    20

(2) INFORMATION FOR SEQ ID NO: 15:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 15:

GCACGCTCTG GAACAGATTC TGGA                                               24

(2) INFORMATION FOR SEQ ID NO: 16:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 16:

ATGAGGAACA GCAACCTTCA CAGC                                               24

(2) INFORMATION FOR SEQ ID NO: 17:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 17:

```
        TCACTCTTGT CGCCCAGATT                                                   20
```

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 18:

```
        TATAGCGGTA GGGGAGATGT                                                   20
```

(2) INFORMATION FOR SEQ ID NO: 19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 19:

```
       TGCAAGGAGA AAGAGAGACT GA                                                 22
```

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 20:

```
       AACAGGACCA CAGGCTCCTA                                                    20
```

(2) INFORMATION FOR SEQ ID NO: 21:

(i) SEQUENCE CHARACTERISTICS:
        (A) LENGTH: 18 base pairs
        (B) TYPE: nucleic acid
        (C) STRANDEDNESS: single

```
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 21:

CAGACGCCGG GACACAAG                                                18

(2) INFORMATION FOR SEQ ID NO: 22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 22:

TACTGGTCCT GCTGGGCTG                                               19

(2) INFORMATION FOR SEQ ID NO: 23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 23:

GTCAGTATTA CCCTGTTACC A                                            21

(2) INFORMATION FOR SEQ ID NO: 24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>
```

(vi) ORIGINAL SOURCE:

(xi) SEQUENCE DESCRIPTION: SEQ ID NO: 24:

GTTGAGGATT TTTGCATCAG T                                             21

(2) INFORMATION FOR SEQ ID NO: 25:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 25:

CTTCCCAGGC CTGCAGTTTG CCCATC                                        26

(2) INFORMATION FOR SEQ ID NO: 26:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 26:

GAACGGGGCT CGAAGGGTCC TTGTAGC                                       27

(2) INFORMATION FOR SEQ ID NO: 27:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 27:

CACCAGTCTC AACACATCAC CATC                                          24

(2) INFORMATION FOR SEQ ID NO: 28:

(i) SEQUENCE CHARACTERISTICS:

```
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 28:

CCTCCAGTGG GTGGGGAAAT GCTC                                            24

(2) INFORMATION FOR SEQ ID NO: 29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 29:

TCCGCGAAGT GATCCAGAAC                                                 20

(2) INFORMATION FOR SEQ ID NO: 30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 30:

CTTGGGGAGA ACCATCCTCA                                                 20

(2) INFORMATION FOR SEQ ID NO: 31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO
```

(v) FRAGMENT TYPE: <Unknown>

(vi) ORIGINAL SOURCE:

(xi) SEQUENCE DESCRIPTION: SEQ ID NO: 31:

AACACCCCTA ATTCACCACT                                                  20

(2) INFORMATION FOR SEQ ID NO: 32:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 32:

ATGATTCCAC AAGATGGCAG                                                  20

(2) INFORMATION FOR SEQ ID NO: 33:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 33:

CCATAGGTTT TGAACTCACA G                                                21

(2) INFORMATION FOR SEQ ID NO: 34:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 34:

CTTCTCAGAT CCTCTGACAC                                                  20

(2) INFORMATION FOR SEQ ID NO: 35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 35:

TCCAGAATCT GTTCCAGAGC GTGC                                      24

(2) INFORMATION FOR SEQ ID NO: 36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 36:

GCTGTGAAGG TTGCTGTTCC TCAT                                      24

(2) INFORMATION FOR SEQ ID NO: 37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 37:

AATCTGGGCG ACAAGAGTGA                                          20

(2) INFORMATION FOR SEQ ID NO: 38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA

```
        (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 38:

ACATCTCCCC TACCGCTATA                                                  20

(2) INFORMATION FOR SEQ ID NO: 39:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 39:

TCAGTCTCTC TTTCTCCTTG CA                                               22

(2) INFORMATION FOR SEQ ID NO: 40:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 40:

TAGGAGCCTG TGGTCCTGTT                                                  20
```

DETECTION OF HYPERMUTABLE NUCLEIC ACID SEQUENCE IN TISSUE AND BODY FLUIDS

RELATED APPLICATION

This application is a continuation of U.S. Ser. No. 08/854,727, filed May 12, 1997, now U.S. Pat. No. 5,935,787 which is a file wrapper continuation of U.S. Ser. No. 08/299,477, filed Aug. 31, 1994, now abandoned.

BACKGROUND OF THE INVENTION

1. Field of the Invention

The present invention relates generally to detection of a target nucleic acid sequence and specifically to detection of a cell proliferative disorder associated with a hypermutable nucleic acid sequence in a sample.

2. Description of Related Art

Mammalian genomes consist of unique DNA sequences interspersed with moderately and highly repetitive DNA sequences. Gene mapping by meiotic linkage analysis has traditionally been carried out using variations in unique sequence DNA, such as restriction fragment length polymorphisms (Botstein, et al., *Am. J. Hum. Genet.*, 32:314–331, 1980), as genetic markers. Recently, variations in the repetitive sequence elements such as minisatellite or variable number tandem repeat (VNTR) sequences (Jeffreys, et al., *Nature*, 314:67–73, 1985; Nakamura, et al., *Science*, 235:1616–1622, 1987), and microsatellite or variable simple sequence motifs (VSSM) (Litt and Luty, *Am. J. Hum. Genet*, 44:397–401, 1989; Weber and May, *Am. J. Hum. Genet.*, 44:388–396, 1989) have been found to be useful for linkage studies. One advantage to the use of repetitive sequence variations rather than unique sequence variations is the apparently greater number of alleles present in normal populations when compared to restriction fragment length polymorphisms (RFLPs). A second advantage is the ability to readily detect sequence length variations using the polymerase chain reaction to facilitate the rapid and inexpensive analysis of large numbers of DNA samples.

Microsatellite elements consist of simple mono-, di-, or tri- nucleotide sequences where alleles differ by one or more repeat units (Luty, et al., *Am.J. Hum. Genet.*, 46:776–783, 1990; Tautz, et al., *Nature*, 322:652–656, 1986; Weber and May, *Am. J. Hum. Genet.*, 44:388–396, 1989). Minisatellites, or VNTR sequences, typically have a repeat unit of 20 to several hundred nucleotides and alleles differ by as little as one repeat unit. Among simple sequences, the $(TG)_n$ or $(CA)_n$ repeat elements have recently proven extremely useful for meiotc mapping since (1) they are abundant in the genome, (2) display a large number of different alleles, and (3) can be rapidly assayed using the polymerase chain reaction (Litt and Luty, *Am. J. Hum. Genet.*, 44:397–401, 1989; Weber and May, *Am. J. Hum. Genet.*, 44:388–396, 1989).

A number of other short sequence motifs have been found in mammalian genomes (Hellman, et al., *Gene,* 68:93–100, 1988; Knott, et al., *Nuc. Acids Res.,* 14:9215–9216, 1986; Litt and Luty, *Am. J. Hum. Genet.,* 44:397–401, 1989; Milstein, et al., *Nuc. Acids Res.,* 12:6523–6535, 1984; Stoker, et al., *Nuc. Acids Res.,* 13:4613–4621, 1985; Vassart, et al., *Science,* 233:683–684, 1987; and Vergnaud, *Nuc. Acids Res.,* 17:7623–7630, 1989), and avian genomes (Gyllensten, et al., *Nuc. Acids Res.,* 17:2203–2214, 1989; Longmire, et al., *Genomics,* 2:14–24, 1988) and are thought to accumulate by DNA slippage during replication (Tautz, et al., *Nature,* 322:652–656, 1986) or unequal recombination events (Wolff, et al., *Genomics,* 5:382–384, 1989). Many of these repeat elements display a high degree of genetic variation and, thus, are also useful for meiotic and mitotic mapping.

The VNTR sequence isolated by Jeffreys, (supra) contains an invariant core sequence GGGCAGGAXG which bears some similarities to the chi sequence of phage lambda (Wolff, et al., *Genomics,* 5:382–384, 1989) and is detected by a restriction fragment of bacteriophage M13 (Vassart, et al., *Science,* 233:683–684, 1987). Similar repeat elements have been detected by Nakamura, et al. (*Science,* 235:1616–1622, 1987) and contain a similar, but distinctive, common core unit GGG--GTGGGG. Elements of this type occur within several known gene sequences including the β globin locus. Similar VNTR elements have been described within the apolipoprotein B (Boerwinkle, et al., *Proc. Natl. Acad. Sci. USA,* 86:212–216, 1989; Knott, et al., *Nuc. Acids Res.,* 14:9215–9216, 1986) and collagen type II genes (Stoker, et al., *Nuc. Acids Res.,* 13:4613–4621, 1985) and contain a distinct AT-rich motif. Though a physiological function for repetitive elements of this type has not been defined, they have been suggested as potential hot spots for chromosome recombination (DeBustros, et al., *Proc. Natl. Acad. Sci. USA,* 85:5693–5697, 1988) or elements important for the control of gene expression (Hellman, et al., *Gene,* 68:93–100, 1988; Milstein, et al., *Nuc. Acids Res.,* 12:6523–6535, 1984).

Microsatellites represent a very common and highly polymorphic class of genetic elements in the human genome. Microsatellite markers containing repeat sequences have been used for primary gene mapping and linkage analysis as described (Weber, et al., *Am. J. Human Genet.,* 44:388, 1989). PCR amplification of these repeats allows rapid assessment for loss of heterozygosity (LOH) and can greatly simplify procedures for mapping tumor suppressor genes (Ruppert, et al., *Cancer Res.* 53:5093, 1993; van der Riet, et al., *Cancer Res.,* 54:1156, 1994). More recently, microsatellites have been used to identify specific mutations in certain inherited disorders including Huntington's disease (HD), fragile X chromosome (FX), myotonic dystrophy (MD), spinocerebellar ataxia type I (SCA1), spino-bulbar muscular dystrophy (SBMA) and hereditary dentatorubral-pallidoluysian atrophy (DRPLA) (The Huntington's Disease Collaborative Research Group., *Cell,* 72:971, 1993; E. J. Kremer, et al., *Science,* 252:1711, 1991; G. Imbert, et al., *Nature Genet.,* 4:72, 1993); H. T. Orr, et al., *Nature Genet.,* 4:221, 1993); V. Biancalana, et al., *Hum. Mol. Genet.,* 1:255, 1992, M-Y,. Chung, et al., *Nature Genet.,* 5:254, 1993, R. Koide, et al., *Nature Genet.,* 6:9, 1994).

Microsatellite instability has recently been described in human cancers. For example, microsatellite instability has been reported to be an important feature of tumors from hereditary non-polyposis colorectal carcinoma (HNPCC) patients (Peltomäki, et al., *Science,* 260:810, 1993; Aaltonen, et al., *Science,* 260:812, 1993; Thibodeau, et al., *Science,* 260:816, 1993). Moreover, microsatellite instability, demonstrated by expansion or deletion of repeat elements has been reported in colorectal, endometrial, breast, gastric, pancreatic, bladder neoplastic tissues (J. I. Risinger, et al., *Cancer Res.,* 53:5100, 1993; H-J. Han, et al., *Cancer Res.,* 53:5087, 1993; P. Peltomäki, et al., *Cancer Res.,* 53:5853, 1993; M. Gonzalez-Zulueta, et al., *Cancer Res.,* 53:5620, 1993), and recently in SCLC. In HNPCC patients, this genetic instability is due to inherited and somatic mutations of a critical mismatch repair gene (hMSH-2). Mutations of hMLH-1 and other critical mismatch repair genes may also be responsible for the instability detected in HNPCC patients.

Cancer remains a major cause of mortality worldwide, and despite advancements in diagnosis and treatment, the overall survival rate has not improved significantly in the past twenty years. There remains an unfulfilled need for a more sensitive means of early diagnosis. Typical assays to detect rare infiltrating tumor cells in clinical samples utilize amplification methods that require additional cloning steps and synthesis of a large number of oligomer specific probes to detect a wide variety of oncogenic mutations for each tumor type (Sidransky, et al., Science, 252:706, 1991; Sidransky, et al., Science, 256:102, 1992). The present invention provides a sensitive assay to detect a variety of cancers using hypermutable microsatellite markers and an amplification strategy which eliminates the need for additional cloning steps.

SUMMARY OF THE INVENTION

The present invention provides a fast, reliable, sensitive screening method for the detection of a cell proliferative disorder in various clinical samples. The invention utilizes amplification of microsatellite nucleic acid (small repeat sequences) to detect a clonal population of cells in a clinical sample.

The invention is based on the unexpected finding that microsatellite alterations are detectable as a clonal population of cells in the DNA of cytologic clinical samples. These samples include urine, sputum, and histopathologic margins obtained from cancer patients.

The invention provides a method for detecting a mammalian cell proliferative disorder (ie., neoplasia) associated with a hypermutable mammalian target nucleic acid in a specimen, comprising isolating the nucleic acid present in the specimen and detecting the presence of the hypermutable target nucleic acid, typically following amplification of the nucleic acid.

In one embodiment, the amplification step in the method of the invention is performed as a multiplex reaction. Therefore, instead of performing multiple amplification reactions to identify each clonal alteration, primers for different markers are combined in one simple amplification reaction, enhancing the identification of a large proportion of cell proliferative disorders.

DETAILED DESCRIPTION OF THE INVENTION

Figure 1:
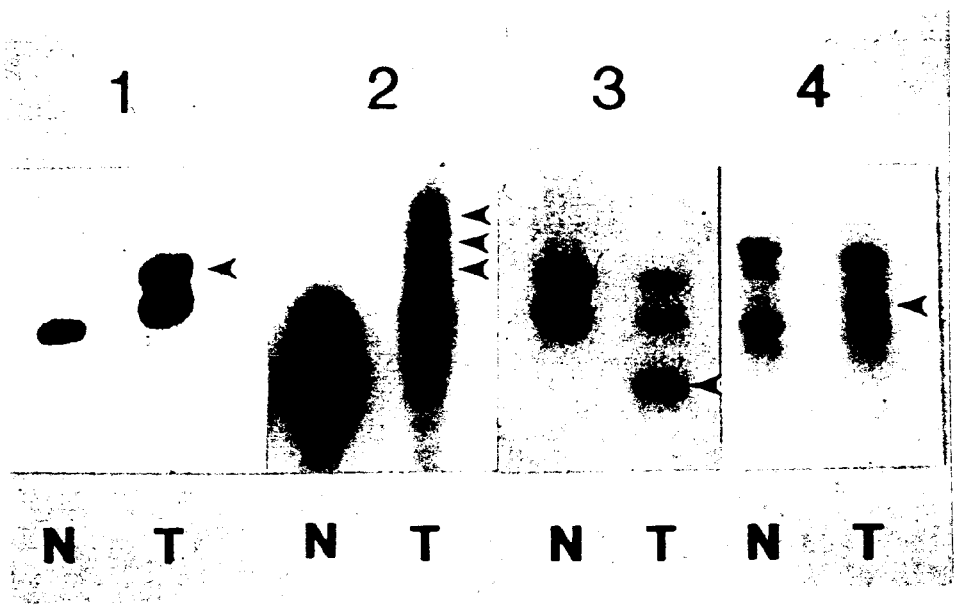
FIG. 1 shows a denaturing acrylamide gel of normal (N) and tumor (T) DNA from lane 1, B17 (TCC) (marker FGA); lane 2, L21 (SCLC) (marker AR); lane 3, B30 (TCC) (marker UT762); and lane 4, L5 (SCLG) (marker D14S50).

The present invention relates to a method of detecting a cell proliferative disorder associated with a target nucleic acid having a hypermutable nucleotide sequence. Preferably, the hypermutable nucleotide sequence of the invention is a microsatellite DNA sequence. Microsatellite alterations in various cancer lesions, for example, can be detected by using known microsatellite repeat markers. A combination of repeat markers can be utilized in the method of the invention to identify a large percentage of cell proliferative disorders or neoplasias even if the neoplastic cells comprise only a small fraction of the clinical sample.

As used herein, the term "hypermutable" refers to a nucleic acid sequence that is susceptible to instability, thus resulting in nucleic acid alterations. Such alterations include the deletion and addition of nucleotides. The hypermutable sequences of the invention are preferably microsatellite DNA sequences which, by definition, are small tandem repeat DNA sequences.

The hypermutable nucleic acid may be a neoplastic nucleic acid sequence. The term "neoplastic" nucleic acid refers to a nucleic acid sequence which directly or indirectly is associated with or causes a neoplasm. The method of the invention is applicable to detection of hypermutable nucleotide sequences associated with benign as well as malignant tumors. The method can be used to detect any hypermutable nucleotide sequence, regardless of origin, as long as the sequence is detectably present in a specimen. The specimen can be blood, urine, sputum, bile, stool, cervical smears, saliva, tears, cerebral spinal fluid, regional lymph node and histopathologic margins, and any bodily fluid that drains a body cavity or organ. For example, neoplasia of regional lymph nodes associated with a primary mammary tumor can be detected utilizing the method of the invention. The term "regional lymph node" refers to lymphoid tissue forming lymphoid organs or nodes which are in close proximity to the primary tumor. For example, regional lymph nodes in the case of head and neck carcinomas include cervical lymph nodes, prelaryngeal lymph nodes, pulmonary juxtaesophageal lymph nodes and submandibular lymph nodes. Regional lymph nodes for mammary tissue carcinomas include the axillary and intercostal nodes. The term "external to a primary neoplasm" means that the specimen is taken from a site other than directly from the primary neoplasm itself. Such specimen may be useful in evaluating whether metastasis of the primary neoplasm has occurred.

The method can also be used to detect a hypermutable nucleic acid sequence associated with a primary tumor by assaying the surrounding tumor margin. As used herein the term "tumor margin" refers to the tissue surrounding a discernible tumor. In the case of surgical removal of a solid tumor, the tumor margin is the tissue cut away with the discernible tumor that usually appears to be normal to the naked eye. More particularly, as used herein, "margin" refers to the edge, border, or boundary of a tumor. The margin generally extends from about 0.2 cm to about 3 cm from the primary tumor but can be greater depending upon the size of the primary solid tumor.

In its broadest sense, the present invention allows the detection of any hypermutable target nucleic acid sequence of diagnostic or therapeutic relevance, where the target nucleic acid sequence is present in a tissue sample. The target nucleotide sequence may be, for example, a restriction fragment length polymorphism (RFLP), nucleotide deletion, nucleotide addition, or any other mammalian nucleic acid sequence of interest in such tissue specimens. Preferably, the microsatellite, hypermutable nucleic acid of the invention contains nucleic acid deletions or additions.

The hypermutable microsatellites most preferred in the method of the invention comprises the sequence $(X)_n$, wherein X is the number of nucleotides in the repeat sequence and is greater than or equal to 1, preferably greater than or equal to 2, and most preferably greater than or equal to 3 and wherein n is the number of repeats and is greater than or equal to 2, and preferably from 4 to 6. Preferably, when X is 2, the nucleotide sequence is TC. Preferably, when X is 3, the nucleotide sequence is selected from AGC, TCC, CAG, CAA, and CTG. Preferably when X is 4, the nucleotide sequence is selected from AAAG, AGAT and TCTT.

The hypermutable nucleic acid sequence is preferably associated with a known locus. For example, hypermutable microsatellite alterations may be detected using a marker selected from ARA (chromosome X), D14S50 (chromosome 14), AR (chromosome X), MD (chromosome 19), SAT (chromosome 6), DRPLA (chromosome 12), ACTBP2 (chromosome 6), FGA (chromosome 4), D4S243 (chromosome 4), and UT762 (chromosome 21). Tandem repeat sequences have been identified as associated with Huntington's disease (HD), fragile X syndrome (FX), myotonic dystrophy (MD), spinocerebellar ataxia type I (SCA1), spino-bulbar muscular dystrophy, and hereditary dentatorubralpallidoluysian atrophy (DRPLA). When the nucleotide sequence of X is larger, it is more likely that the microsatellite locus will have alterations, e.g., a trinucleotide repeat is more likely to have deletions or additions than a dinucleotide repeat. Thus, in the present invention, it has been found that 8% of 25 trinucleotide or tetranucleotide markers displayed microsatellite alternations per 100 tumor specimens examined, whereas only 0.7% of 83 dinucleotide microsatellite markers were found to contain alterations. In addition, it has been found that a regular repeat, such as AAT AAT AAT is more likely to be hypermutable than a sequence which contains interruptions in the repeat sequence, e.g., AAT GAC AAT AAT. Consequently, those of ordinary skill in the art can readily identify other hypermutable target nucleic acid sequences by considering the size of the candidate sequence and whether the sequence is uninterrupted without resorting to undue experimentation. Other microsatellite markers will be known by the criteria described herein and are accessible to those of skill in the art. Smaller microsatellite markers including dinucleotide and mononucleotide repeats may be hypermutable and useful for this analysis.

The present invention identifies hypermutable target sequences, preferably microsatellite loci, that are unique to a particular cellular proliferative disorder, primary tumor, or metastatic sites derived from the primary tumor. In the tumor cell, the hypermutable nucleotide sequence is evidenced by nucleic acid deletions or expansion of repeat sequences as compared to a normal cell; therefore, it is possible to design appropriate diagnostic techniques directed to the specific sequence and to design therapeutic strategies once the sequence is identified.

The term "cell-proliferative disorder" denotes benign as well as malignant cell populations which morphologically often appear to differ from the surrounding tissue. For example, the method of the invention is useful in detecting malignancies of the various organ systems, such as, for example, lung, breast, lymphoid, gastrointestinal, and genito-urinary tract as well as epithelial carcinomas which include malignancies such as most colon cancers, renal-cell carcinoma, prostate cancer, non-small cell carcinoma of the lung, cancer of the small intestine, cancer of the head and neck, stomach cancer, bladder cancer, kidney cancer, cervical cancer, cancer of the esophagus and any other organ type that has a draining fluid or tissue accessible to analysis. The method of the invention is also useful in detecting non-malignant cell-proliferative diseases such as colon adenomas, hyperplasia, dysplasia and other "pre-malignant" lesions. Essentially, any disorder which is etiologically linked to a hypermutable microsatellite locus would be considered susceptible to detection.

When it is desired to amplify the target nucleotide sequence before detection, such as a hypermutable nucleotide sequence, this can be accomplished using oligonucleotides that are primers for amplification. The oligonucleotide primers are designed based upon identification of the nucleic acid sequence of the flanking regions contiguous with the hypermutable nucleotide sequence. For example, in the case of hypermutable microsatellite nucleic acid sequences, oligonucleotide primers comprise sequences which are capable of hybridizing with nucleotide sequences flanking the loci of mutations, such as the following nucleotide sequences:

a. 5'-CTT GTG TCC CGG CGT CTG-3' (SEQ ID NO:1);

b. 5'-C AGC CCA GCA GGA CCA GTA-3' (SEQ ID NO:2);

c. 5'-TGG TAA CAG TGG AAT ACT GAC-3' (SEQ ID NO:3);

d. 5'-ACT GAT GCA AAA ATC CTC AAC-3' (SEQ ID NO:4);

e. 5'-GA TGG GCA AAC TGC AGG CCT GGG AAG-3' (SEQ ID NO:5);

f. 5'-GCT ACA AGG ACC CTT CGA GCC CCG TTC-3' (SEQ ID NO:6);

g. 5'-GAT GGT GAT GTG TTG AGA CTG GTG-3' (SEQ ID NO:7);

h. 5'-GAG CAT TTC CCC ACC CAC TGG AGG-3' (SEQ ID NO:8);

i. 5'-GTT CTG GAT CAC TTC GCG GA-3' (SEQ ID NO:9);

j. 5'-TGA GGA TGG TTC TCC CCA AG-3' (SEQ ID NO:10);

k. 5'-AGT GGT GM TTA GGG GTG TT-3' (SEQ ID NO:11);

l. 5'-CTG CCA TCT TGT GGA ATC AT-3' (SEQ ID NO:12);

m. 5'-CTG TGA GTT CAA AAC CTA TGG-3' (SEQ ID NO:13);

n. 5'-GTG TCA GAG GAT CTG AGA AG-3' (SEQ ID NO:14);

o. 5'-GCA CGC TCT GGA ACA GAT TCT GGA-3' (SEQ ID NO:15);

p. 5'-ATG AGG AAC AGC AAC CTT CAC AGC-3' (SEQ ID NO:16);

q. 5'-TCA CTC TTG TCG CCC AGA TT-3' (SEQ ID NO:17);

r. 5'-TAT AGC GGT AGG GGA GAT GT-3' (SEQ ID NO:18);

s. 5'-TGC AAG GAG AAA GAG AGA CTG A-3' (SEQ ID NO:19);

t. 5'-AAC AGG ACC ACA GGC TCC TA-3' (SEQ ID NO:20); and u. sequences complementary to sequences a. through t.

Primers that hybridize to these flanking sequences are, for example, the following:

a. 5'-CAG ACG CCG GGA CAC AAG-3' (SEQ ID NO:21);
b. 5'-TAC TGG TCC TGC TGG GCT G-3' (SEQ ID NO:22);
c. 5'-GTC AGT ATT ACC CTG TTA CCA-3' (SEQ ID NO:23);
d. 5'-GTT GAG GAT TTT TGC ATC AGT-3' (SEQ ID NO:24);
e. 5'-CTT CCC AGG CCT GCA GTT TGC CCA TC-3' (SEQ ID NO:25);
f. 5'-GAA CGG GGC TCG AAG GGT CCT TGT AGC-3' (SEQ ID NO:26);
g. 5'-CAC CAG TCT CAA CAC ATC ACC ATC-3'(SEQ ID NO:27);
h. 5'-CCT CCA GTG GGT GGG GAA ATG CTC-3' (SEQ ID NO:28);
i. 5'-TCC GCG AAG TGA TCC AGA AC-3'(SEQ ID NO:29);
j. 5'-CTT GGG GAG AAC CAT CCT CA-3'(SEQ ID NO:30);
k. 5'-AAC ACC CCT AAT TCA CCA CT-3'(SEQ ID NO:31);
l. 5'-ATG ATT CCA CAA GAT GGC AG-3'(SEQ ID NO:32);
m. 5'-CCA TAG GTT TTG AAC TCA CAG-3'(SEQ ID NO:33);
n. 5'-CTT CTC AGA TCC TCT GAC AC-3'(SEQ ID NO:34);
o. 5'-TCC AGA ATC TGT TCC AGA GCG TGC-3'(SEQ ID NO:35);
p. 5'-GCT GTG AAG GTT GCT GTT CCT CAT-3'(SEQ ID NO:36);
q. 5'-AAT CTG GGC GAC AAG AGT GA-3'(SEQ ID NO:37);
r. 5'-ACA TCT CCC CTA CCG CTA TA-3'(SEQ ID NO:38);
s. 5'-TCA GTC TCT CTT TCT CCT TGC A-3' (SEQ ID NO:39);
t. 5'-TAG GAG CCT GTG GTC CTG TT-3' (SEQ ID NO:40); and
u. sequences complementary to sequences a. through t.

One skilled in the art will be able to generate primers suitable for amplifying target sequences of additional nucleic acids, such as those flanking loci of known microsatellite sequences, using routine skills known in the art and the teachings of this invention.

In general, the primers used according to the method of the invention embrace oligonucleotides of sufficient length and appropriate sequence which provide specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15–22 or more nucleotides, although it may contain fewer nucleotides as long as the primer is of sufficient specificity to allow essentially only the amplification of the specifically desired target nucleotide sequence (i.e., the primer is substantially complementary).

Experimental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition.

Primers used according to the method of the invention are designed to be "substantially" complementary to each strand of mutant nucleotide sequence to be amplified. Substantially complementary means that the primers must be sufficiently complementary to hybridize with their respective strands under conditions which allow the agent for polymerization to function. In other words, the primers should have sufficient complementarily with the flanking sequences to hybridize with and permit amplification of the nucleotide sequence. Preferably, the 3' terminus of the primer that is extended has perfectly base paired complementarity with the complementary flanking strand.

Oligonucleotide primers used according to the invention are employed in any amplification process that produces increased quantities of target nucleic acid. Typically, one primer is complementary to the negative (−) strand of the mutant nucleotide sequence and the other is complementary to the positive (+) strand. Annealing the primers to denatured nucleic acid followed by extension with an enzyme, such as the large fragment of DNA Polymerase I (Klenow) or Taq DNA polymerase and nucleotides or ligases, results in newly synthesized (+) and (−) strands containing the target nucleic acid. Because these newly synthesized nucleic acids are also templates, repeated cycles of denaturing, primer annealing, and extension results in exponential production of the region (i.e., the target hypermutable nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

The oligonucleotide primers for use in the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22:1859–1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

The nucleic acid from any specimen, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, including messenger RNA (mRNA), wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The mutant nucleotide sequence to be amplified may be a fraction of a larger molecule or can be present initially as a discrete molecule, such that the specific sequence constitutes the entire nucleic acid. It is not necessary that the sequence to be amplified be present initially in a pure form; it may be a minor fraction of a complex mixture, such as contained in whole human DNA.

Where the target neoplastic nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means; the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP which is known to denature DNA. The reaction conditions suitable for strand separation of nucleic acids with helicases are described by Kuhn Hoffmann-Berling (*CSH-Quantitative Biology*, 43:63, 1978) and techniques for using RecA are reviewed in C. Radding (*Ann. Rev. Genetics*, 16:405–437, 1982).

If the nucleic acid containing the target nucleic acid to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates. Generally synthesis occurs in a buffered aqueous solution, preferably at a pH of 7–9, most preferably about 8. Preferably, a molar excess (for genomic nucleic acid, usually about $10^8:1$ primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

In some amplification embodiments, the substrates, for example, the deoxyribonucleotide triphosphates dATP, dCTP, dGTP, and dTTP, are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. The agent for polymerization may be any compound or system which will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, other available DNA polymerases, polymerase muteins, reverse transcriptase, ligase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each mutant nucleotide strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above. In any event, the method of the invention is not to be limited to the embodiments of amplification which are described herein.

The newly synthesized mutant nucleotide strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleotides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target hypermutable nucleotide sequence to the extent necessary for detection. The amount of the hypermutable nucleotide sequence produced will accumulate in an exponential fashion.

In one embodiment of the invention, a combination of hypermutable microsatellite markers are amplified in a single amplification reaction. The markers are "multiplexed" in a single amplification reaction, for example, by combining primers for more than one locus. For example, DNA from a urine sample is amplified with three different randomly labelled primer sets such as FGA, ACTBP2 and AR, in the same amplification reaction. The products are ultimately separated on a denaturing acrylamide gel and then exposed to film for visualization and analysis.

The amplified product may be detected by Southern blot analysis, without using radioactive probes. In such a process, for example, a small sample of DNA containing a very low level of microsatellite hypermutable nucleotide sequence is amplified, and analyzed via a Southern blotting technique. The use of non-radioactive probes or labels is facilitated by the high level of the amplified signal. In a preferred embodiment of the invention, one nucleoside triphosphate is radioactively labeled, thereby allowing direct visualization of the amplification product by autoradiography. In another embodiment, amplification primers are fluorescent labelled and run through an electrophoresis system. Visualization of amplified products is by laser detection followed by computer assisted graphic display.

Nucleic acids having a hypermutable microsatellite sequence detected in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

In another embodiment of the invention, purified nucleic acid fragments that contain oligonucleotide sequences of 10–50 bases from microsatellite loci, are radioactively labelled. The labelled preparations are used to probe nucleic acid by the Southern hybridization technique. Nucleotide fragments from a specimen, before or after amplification, are separated into fragments of different molecular masses by gel electrophoresis and transferred to filters which bind nucleic acid. After exposure to the labelled probe, which will hybridize to nucleotide fragments containing target nucleic acid sequences, binding of the radioactive probe to target nucleic acid fragments is identified by autoradiography (see *Genetic Engineering*, 1, ed. Robert Williamson, Academic Press, (1981), 72–81).

Probes for microsatellite loci of the present invention can be used for examining the distribution of the specific fragments detected, as well as the quantitative (relative) degree of binding of the probe for determining the occurrence of specific strongly binding (hybridizing) sequences, thus indicating the presence of extensive alterations in a particular locus.

For the most part, the probe (or amplifcation primer) will be labelled with an atom or inorganic radical, most commonly using radionuclides, but also perhaps heavy metals. Conveniently, a radioactive label may be employed. Radioactive labels include $^{32}P$, $^{125}I$, $^{3}H$, $^{14}C$, $^{35}S$, or the like. Any radioactive label may be employed which provides for an adequate signal and has sufficient half-life. Other labels include ligands, which can serve as a specific binding pair member for a labelled ligand, and the like. A wide variety of labels have been employed in immunoassays which can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an $\alpha$-$^{32}P$-dNTP or terminal phosphate hydrolysis with alkaline phosphatase followed by labeling with radioactive $^{32}P$ employing $\gamma$-$^{32}P$-ATP and T4 polynucleotide kinase. Alternatively, nucleotides can be synthesized where one or more of the elements present are replaced with a radioactive isotope, e.g., hydrogen with tritium. If desired, complementary labelled strands can be used as probes to enhance the concentration of hybridized label.

Where other radionuclide labels are involved, various linking groups can be employed. A terminal hydroxyl can be esterified, with inorganic acids, e.g., $^{32}P$ phosphate, or $^{14}C$ organic acids, or else esterified to provide linking groups to the label. Alternatively, intermediate bases may be substituted with activatable linking groups which can then be linked to a label.

Enzymes of interest as reporter groups will primarily be alkaline phosphatase, hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include, for example, luciferin, and 2,3-dihydrophtha-lazinediones (e.g., luminol).

An oligomer probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports which can be used in the method of the invention.

The nucleic acid from a specimen is spotted or spread onto a filter to provide a plurality of individual portions. The filter is an inert porous solid support, e.g., nitrocellulose or nylon membranes. Any mammalian cells present in the specimen are treated to liberate their nucleic acid. The lysing and denaturation of nucleic acid, as well as the subsequent washings, can be achieved with an appropriate solution for a sufficient time to lyse the cells and denature the nucleic acid. Other denaturation agents include elevated temperatures, organic reagents (e.g., alcohols, amides, amines, ureas, phenols and sulfoxides) or certain inorganic ions (e.g., thiocyanate and perchlorate). Alternatively, nucleic acid can be isolated from blood using standard procedures with the DNA subsequently applied to the membrane.

After denaturation, the filter is washed in an aqueous buffered solution, such as Tris, generally at a pH of about 6 to 8, usually 7. One or more washings may be involved, conveniently using the same procedure as employed for the lysing and denaturation. After the lysing, denaturing, and washes have been accomplished, the nucleic acid spotted filter is dried at an elevated temperature, generally from about 50° C. to 70° C. or UV-crosslinked (for nylon membranes). Under this procedure, the nucleic acid is fixed in position and can be assayed with the probe when convenient.

Pre-hybridization may be accomplished by incubating the filter at a mildly elevated temperature for a sufficient time with the hybridization solution without the probe to thoroughly wet the filter. Various hybridization solutions may be employed, comprising from about 20% to 60% volume, preferably 30%, of an inert polar organic solvent or aqueous hybridization solutions.

The particular hybridization technique is not essential to the invention. Other hybridization techniques are well known or easily ascertained by one of ordinary skill in the art. As improvements are made in hybridization techniques they can readily be applied in the method of the invention.

The amount of labelled probe which is present in the hybridization solution will vary widely, depending upon the nature of the label, the amount of the labelled probe which can reasonably bind to the filter, and the stringency of the hybridization. Generally, substantial excess over stoichiometric concentrations of the probe will be employed to enhance the rate of binding of the probe to the fixed target nucleic acid.

Various degrees of stringency of hybridization may be employed. The more stringent the conditions, the greater the complementarity that is required for hybridization between the probe and the single stranded target nucleic acid sequence for duplex formation. Stringency can be controlled by temperature, probe concentration, probe length, ionic strength, time, and the like. Conveniently, the stringency of hybridization is varied by changing the polarity of the reactant solution by manipulating the concentration of formamide in the range of 20% to 50%. Temperatures employed will normally be in the range of about 20° C. to 80° C., usually 30° C. to 75° C. (see, generally, *Current Protocols in Molecular Biology,* Ausubel, ed., Wiley & Sons, 1989). Alternatively, stringency can be controlled when the non-annealed probe is washed off.

After the filter has been contacted with a hybridization solution at a moderate temperature for a period of time sufficient to allow hybridization to occur, the filter is then introduced into a second solution having sodium chloride, sodium citrate and sodium dodecylsulfate. The time for which the filter is maintained in the second solution may vary from five minutes to three hours or more. The second solution and the temperature (generally 5° C. below the melting temperature) determines the stringency, dissolving duplexes, and short complementary sequences. For short oligonucleotide probes, the melting temperature can be standarized according to probe length, rather than sequence, by including tetramethyl ammonium chloride in the wash solution (DiLella and Woo, *Meth. Enzymol.,* 152:447, 1987). The filter may now be assayed for the presence of duplexes in accordance with the nature of the label. Where the label is radioactive, the filter is dried and exposed to X-ray film.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method.

For example, one of the container means may comprise amplification primers for a microsatellite locus or a hybridization probe, all of which can be detectably labelled. If present, a second container may comprise a lysis buffer. The kit may also have containers containing nucleotide(s) for amplification of the target nucleic acid sequence which may or may not be labeled, and/or a container comprising a reporter-means, such as a biotin-binding protein, such as avidin or streptavidin, bound to a reporter molecule, such as an enzymatic, florescent, or radionuclide label.

The above disclosure generally describes the present invention. A more complete understanding can be obtained by reference to the following specific examples which are provided herein for purposes of illustration only and are not intended to limit the scope of the invention.

EXAMPLES

During primary mapping studies using 43 dinucleotide markers in over 300 tumors including SCC, non-small cell lung carcinoma (NSCLC), transitional cell carcinoma of the bladder (TCC), and squamous and basal cell skin carcinoma, single somatic alterations were observed in approximately 0.7% of tumor DNA This low rate of "background" alterations in dinucleotide markers is consistent with other studies demonstrating few changes in non-HNPCC-associated tumors (S. N. Thibodeau, et al., *Science,* 260:816, 1993; J. I. Risinger, et al., *Cancer Res.,* 53:5100, 1993; H-J. Han, et al., *Cancer Res.,* 53:5087, 1993); P. Peltomaki, et al., *Cancer Res.,* 53: 5853, 1993); M. Gonzalez-Zulueta, et al., *Cancer Res.,* 53:5620, 1993; R. Wooster, et al., *Nature Gent.,* 6:152, 1994) and germline DNA (J. L. Weber, et al., *Am. J. Human Genet.,* 44:388, 1989), J. Weissenback, et al., *Nature,* 359:794, 1992; (A. J. Jeffreys, et al., *Nature Genet.,* 6:136, 1994). 35 SCC, 20 NSCLC, 10 SCLC, and 32 TCC normal and cancer DNA pairs were tested using tri- and tetranucleotide repeat markers (TABLE 1). Of these, approximately 8% and 20% of tumor DNA had somatic alterations using tri- and tetranucleotide repeat-markers, respectively. Of the nine markers, four (MD, DRPLA, AR (SBMA), and SAT (SCA1)) were associated with neurological disease and have revealed germline expansion of their repeat sequences in affected patients. Because of these germline alterations, it was thought that these markers might be more susceptible to expansion or deletion in tumor DNA as compared with dinucleotide repeat sequences. The other markers were chosen among commercially available tri- or tetranucleotide repeat markers except for UT762 (on human chromosome 21), which was previously reported to have an excess of germline alterations on human chromosome 21 (C. C. Talbot, Jr., et al., *43rd American Society of Human Genetics Meeting,* Abstract, 1993).

Example 1

Primers Utilized for Amplification of Specimen DNA

All tumors were fresh-frozen except for SCLC which was paraffin-embedded. Non-neoplastic tissue was microdissected away to be used as normal DNA. Alternatively, fresh blood was obtained and lymphocytes separated. Tumor and normal tissue was digested with 1% SDS-proteinase K followed by ethanol precipitation to extract DNA. 50 ng of DNA was subject to PCR amplification; the products were run on denaturing acrylamide gels as described previously (P. van der Riet, et al., *Cancer Res.*, 54:1156, 1994), H. Nawroz, P., *Cancer Res.*, 54:1152, 1994; P. Cairns, et al., *Cancer Res.*, 54:1422, 1994).

Primers used to amplify each locus were obtained from Research Genetics, Inc., with the exception of the following loci:

a. 5'-CAG ACG CCG GGA CAC AAG-3' (SEQ ID NO:21);
 b. 5'-TAC TGG TCC TGC TGG GCT G-3' (SEQ ID NO:22);
 c. 5'-GTC AGT ATT ACC CTG TTA CCA-3' (SEQ ID NO:23);
 d. 5'-GTT GAG GAT TTT TGC ATC AGT-3' (SEQ ID NO:24);
 e. 5'-CTT CCC AGG CCT GCA GTT TGC CCA TC-3' (SEQ ID NO:25);
 f. 5'-GAA CGG GGC TCG AAG GGT CCT TGT AGC-3' (SEQ ID NO:26);
 g. 5'-CAC CAG TCT CAA CAC ATC ACC ATC-3'(SEQ ID NO:27);
 h. 5'-CCT CCA GTG GGT GGG GAA ATG CTC-3' (SEQ ID NO:28);
 i. 5'-TCC GCG AAG TGA TCC AGA AC-3'(SEQ ID NO:29);
 j. 5'-CTT GGG GAG AAC CAT CCT CA-3'(SEQ ID NO:30);

Example 2

Detection of Alterations in Microsatellite Loci

Each microsatellite locus was amplified in paired normal/tumor DNA by PCR and labelled products were then run on denaturing acrylamide gels and exposed to film. 29% of head and neck cancers, 5% of NSCLC, 50% of SCLC, and 28% of bladder tumors exhibited microsatellite alterations in at least one susceptible marker (TABLE 1). These genetic alterations were identified as a novel band (or bands) in the tumor DNA lane and were not present in the paired normal DNA lane (FIG. 1). FIG. 1 shows microsatellite alterations in tumor DNA. Normal and tumor DNA were amplified by PCR and run on denaturing acrylamide gels as described (P. van der Riet, supra). Novel bands representing deletion or expansion of tandem repeat sequences were seen in all four tumor lanes as indicated by the arrows. Lane 1) B17 (TCC) with marker FGA on chromosome 4; Lane 2) L21 (SCLC) with marker AR on chromosome X; Lane 3) B30 (TCC) with marker UT762 on chromosome 21; and Lane 4) L5 (SCLC) with marker D14S50 on chromosome 14. (N: normal DNA. T: tumor DNA).

For each case, the amplification was repeated and the alterations reproduced. The frequency of alterations was significantly higher in these tri- or tetranucleotide repeat markers and also appeared to be tumor-type specific (TABLE 1). In TCC, for example, the AR repeat is altered in 3% of tumors whereas 18% of SCC's displayed alterations at this locus. A significant difference in the frequency of alterations between disease and non-disease related tri- and tetranucleotide repeat sequences was not observed suggesting that there might exist a more generalized cellular mechanism for these changes, rather than inherent sequence differences in the repeat regions.

k. 5'-AAC ACC CCT AAT TCA CCA CT-3'(SEQ ID NO:31);
 l. 5'-ATG ATT CCA CAA GAT GGC AG-3'(SEQ ID NO:32);
 m. 5'-CCA TAG GTT TTG AAC TCA CAG-3'(SEQ ID NO:33);
 n. 5'-CTT CTC AGA TCC TCT GAC AC-3'(SEQ ID NO:34);
 o. 5'-TCC AGA ATC TGT TCC AGA GCG TGC-3'(SEQ ID NO:35);
 p. 5'-GCT GTG AAG GTT GCT GTT CCT CAT-3'(SEQ ID NO:36);
 q. 5'-AAT CTG GGC GAC AAG AGT GA-3'(SEQ ID NO:37);
 r. 5'-ACA TCT CCC CTA CCG CTA TA-3'(SEQ ID NO:38);
 s. 5'-TCA GTC TCT CTT TCT CCT TGC A-3' (SEQ ID NO:39);
 t. 5'-TAG GAG CCT GTG GTC CTG TT-3' (SEQ ID NO:40); and
 u. sequences complementary to sequences a. through t.

P. Modrich, *Annu. Rev. Genet.*, 25:229, (1991). Cytological samples were spun at 3000×g for 5', and washed with PBS twice. Cell pellets were digested with 1% SDS-proteinase K, and DNA extracted as described previously (D. Sidransky, et al., *Science*, 252:706, 1991), *Science*, 256:102, 1992; Surgical margin DNA was obtained from slides which were histopathologically negative. Tissue was scraped and placed in xylene to remove excess paraffin. After centrifugation with one quarter volume 70% ethanol, pellets were digested and DNA extracted as described previously (D. Sidransky, supra, R. H. Hruban, supra, L. Mao, supra).

SCLC displayed generalized microsatellite instability similar to that seen in HNPCC-associated tumors and altered a high percentage of all markers including dinucleotides (A. Merlo, et al., supra).

Although widespread microsatellite instability has been found most frequently in HNPCC, other non-HNPCC tumors contain occasional alterations. These changes usually involve only one locus, rather than the multiple loci typically seen in HNPCC patients (A. Merlo, et al., supra; R. Wooster, et al., supra). The widespread instability found in SCLC is an exception, and the genetic basis for this is still unknown. In this study, none of the tumors we tested were HNPCC-associated. Comparison of dinucleotide repeat (29 of 4171 tested) versus tri- or tetranucleotide repeat alterations (44 of 874 tested) in these 97 tumors reveals a significant susceptibility to genetic instability in the larger alleles (p=0.08×10$^{-9}$ by $\chi^2$ analysis). The high frequency of microsatellite alterations found here suggests that certain loci may be inherently more unstable than others. The mechanism producing the altered alleles in these tumors may differ from that described in HNPCC (F. Leach, et al., *Cell*, 75:1215, 1993; R. Fishel, et al., *Cell*, 75:1027, 1993) or could reflect more subtle defects in similar or related repair pathways (P. Modrich, *Annu. Rev. Genet.*, 25:229, 1991). From these data, it appears that occasional microsatellite alterations may be a relatively generally phenomenon in many human cancers with some loci altered in a tumor-type specific manner.

Sidransky, et al., supra). The intensity of the shifted band was approximately 5% of the intensity of the corresponding band in tumor DNA, indicating that only a small population

TABLE 1

FREQUENCY OF MICROSATELLITE ALTERATIONS

| REPEAT SIZE | NAME (CHROMO) | REPEAT SEQUENCE | HEAD AND NECK SCC (n = 35) | NSCLC (n = 23) | SCLC (n = 10) | BLADDER TCC (N = 32) | Total (n = 100) |
|---|---|---|---|---|---|---|---|
| Trinucleotide | ARA (X) | (AGC) | 2 (6%) | 1 (4%) | — | 1 (3%) | 4 (4%) |
| | D14S50 (14) | (TCC) 7, (TC) 9 (AC) 6,G (CA) 12.5 | 1 (3%) | 1 (4%) | 0 | 0 | 2 (2%) |
| | AR (X)* | (CAG) 19 (CAA) | 6 (18%) | 1 (4%) | 4 (40%) | 1 (3%) | 2 (2%) |
| | MD (19)* | (CTG) | 0 | 1 (4%) | — | 2 (6%) | 3 (3%) |
| | SAT (6)* | (CAG) | 4 (11%) | 1 (4%) | — | 1 (3%) | 6 (6%) |
| | DRPLA (12)* | (CAG) | 1 (3%) | 0 | — | 0 | 1 (1%) |
| Tetranucleotide | ACTBP2 (6) | (AAAG) 11, (AAAG) 15 | 1 (3%) | 1 (4%) | 2 (20%) | 3 (9%) | 7 (7%) |
| | FGA (4) | (TCTT) 13 | 2 (6%) | 1 (4%) | 0 | 3 (9%) | 6 (6%) |
| | UT762 (21) | (AAAG) | 0 | 1 (4%) | 4 (40%) | 5 (15%) | 10 (10%) |
| | | Total # of tumors with alterations in ˆlocus | 10 (29%) | 2 (9%) | 5 (50%) | 9 (28%) | 26 (26%) |

Microsatellite alterations for each marker tested a number of alterations detected in each tumor type.
SCC: head and neck squamous cell carcinoma.
NSCLC: non-small cell lung carcinoma.
SCLC: small cell lung carcinoma.
TCC: transitional cell carcinoma of the bladder.
26 of 100 (26%) total tumors displayed alterations in at least one locus.
*Disease related.

Example 3

Detection of Clonal Populations of Tumor-derived Cells

Figures 2A, 2B, 2C:
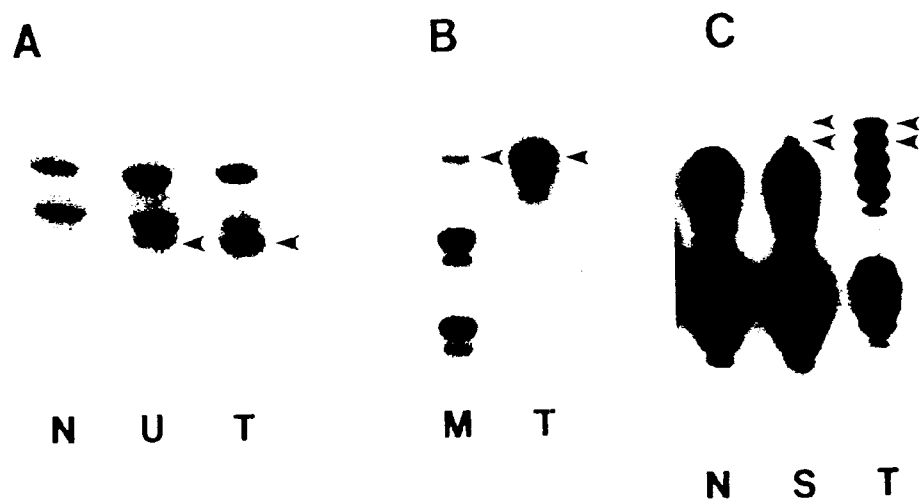
FIGS. 2A–2C shows a denaturing acrylamide gel of Panel A) a urine (U) sample of B27 (TCC) analyzed with marker FGA and compared with normal (N) and tumor (T) tissue DNA; Panel B) histological margin (M) of L31 (NSCLC) screened with AR and compared with tumor tissue; and Panel C) sputum (S) sample of L25 (SCLC) analyzed with CHRNB and compared with normal and tumor tissue DNA.

These clonal microsatellite alterations were studied to see if they could be detected in cytologic samples as tumor-specific markers. To demonstrate this potential clinical application, several corresponding cytological samples that were considered negative for the presence of cancer cells by light microscopy were analyzed. When DNA from bladder tumor B27 was screened with the tetranucleotide marker FGA, a novel band was identified in the tumor lane as compared to normal (FIG. 2A). FIG. 2 shows detection of clonal microsatellite alterations in clinical samples. PCR conditions and gel analysis have been described (P. van der Riet, et al., supra). Novel bands are indicated by arrows. Panel A), The corresponding cytologic urine sample of B27 (TCC) was analyzed using marker FGA and compared with normal and tumor DNA. A novel or "shifted" band is seen in the tumor lane vs. the normal lane and at a lesser, but significant intensity in the urine lane. Panel (B), Lymphocytic DNA was not available from this patient, but a light band is clearly identified in the "negative" histological margin of L31 (NSCLC) which corresponds to the more intense novel band in the tumor lane when screened with marker AR. Panel (C), Amplification of marker CHRNB; the corresponding sputum sample of L25 (SCLC) revealed two light bands consistent with the novel bands in the tumor lane. These bands are not present in the normal DNA. (N: normal DNA, U: urine DNA, T: tumor DNA, M: margin DNA, S: sputum DNA).

DNA obtained from the patient's urine sample before surgery was screened with the same marker, revealing the same novel band at a lower intensity in the urine DNA (D.

of cells in the urine sample was tumor-derived. One patient with SCLC was found to have a novel CHRNB allele in the tumor DNA when compared to normal DNA. When DNA from a corresponding, prospectively collected sputum sample was screened with the marker CHRNB, the identical genetic change in the sputum DNA initially found in the patient's primary SCLC (FIG. 2c). Again, the lower intensity of the novel bands in sputum suggested that only a small fraction of cancer cells was present in the sample. Several histopathologically negative surgical margins were examined (D. Sidransky, et al., supra). The tumor DNA of L29 demonstrates a novel, smaller band at the microsatellite marker IFN, while paired DNA of a histologically negative surgical margin presented the same shifted band at lower intensity (FIG. 2B). This is consistent with the previous observation that undetected infiltrating tumor cells can be identified in surgical margins after "complete" surgical resection with sensitive molecular techniques.

These examples demonstrate the ability to detect clonal populations of tumor-derived cells in cytologic samples and histopathologic tissue. This assay was readily reproducible using other altered markers to test corresponding samples in these cases and paired samples from other patients. Clinical samples from patients without a microsatellite alteration detected in the primary tumor were consistently negative.

Example 4

Sensitivity Determination by Dilution

An obvious problem in screening clinical samples is the need to detect an extremely small number of cancer cells among a large background of normal cells, especially in bodily fluids such as urine and sputum. To demonstrate the sensitivity of the method of the invention, the DNA of bladder tumors B17, which has a larger novel allele, and B27, which has a smaller novel allele were utilized. These two samples were chosen because of our observation that smaller alleles tend to amplify better than larger alleles by PCR. Tumor DNA was diluted with normal, lymphocytic DNA from the same patient and 50 ng of DNA from each dilution was amplified by PCR.

Figure 3A:
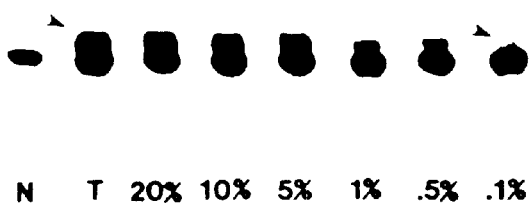
FIGS. 3A–3B shows DNA from patients' lymphocytes (N) amplified with marker FGA at varying dilutions with tumor DNA from 1 in 5 (20%) to 1 in 1000 (0.1%). Novel bands are indicated by an arrow. Panel A, tumor DNA from B17 (TCC); panel B, tumor DNA of B27 (TCC).
Figure 3B:

FIG. 3 shows sensitivity determination by simple dilution. DNA from tumors (T) containing alterations were diluted with the corresponding patients' lymphocyte DNA (N) from 1 in 5 (20%) to 1 in 1000 (0.1%). Samples were then amplified by PCR with marker FGA, separated by denaturing gel electrophoresis and visualized by autoradiography as described (P. van der Riet, et al., supra). Novel bands are indicated by an arrow. Panel (A) shows the novel band seen in the tumor lane of B17 (TCC) is still visible when diluted with its normal corresponding DNA to 0.1%. Similarly in Panel (B), the novel band in the tumor DNA of B27 (TCC) is clearly seen when diluted to 0.5%.

The "shifted" band was seen in the dilution mixture containing only 0.1% of tumor DNA in B17 and 0.5% tumor DNA in B27. These results suggest that this method may potentially detect one cancer cell among 200 to 1000 normal cells, thus proving its potential usefulness as a clinical screening assay.

Example 5

Multiplex PCR Assay for Detection of Hypermutable Nucleic Acid

Microsatellite alterations in HNPCC and SCLC could be detected by using just a few microsatellite repeat markers since these tumors alter a high percentage of all tested alleles. For non-HNPCC tumors, a single well-selected tri- or tetranucleotide repeat marker could potentially identify over 15% of tumors for a particular cancer type. In SCC and TCC, seven selected markers detected over 28% of tumors (TABLE 1). Because the genetic mechanism underlying these occasional alterations is still not known, it is possible that some cancers will not display any alterations regardless of how many markers are tested. Nevertheless, the human genome contains over 100,000 repeat regions and it is very likely that other candidate markers could be identified for this analysis. A combination of repeat markers could be utilized to identify a high percentage of cancer patients; the ability to potentially test several markers in a single PCR reaction could simplify the ultimate screening approach.

DNA from B27 (TCC) and a corresponding urine sample was amplified with three different primers sets (FGA on chromosome 4, ACTBP2 on chromosome 6, and AR on the X chromosome) in the same PCR reaction, separated on denaturing acrylamide gels and exposed to film. The concentration of each primer was diluted to 100 ng/Ig in the final PCR reaction. A novel band in the tumor lane is identical to the corresponding, less intense band in the urine DNA lane. (N: normal DNA, T: tumor DNA, U: urine DNA).

Figure 4:
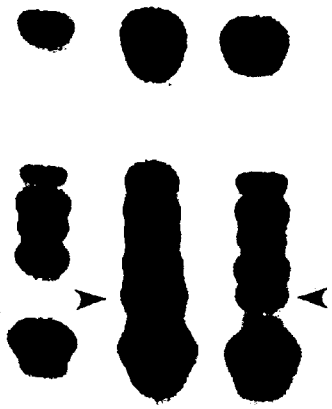
FIG. 4 shows a multiplex PCR assay utilizing DNA from B27 (TCC) and a corresponding urine sample amplified with three different primer sets (FGA, ACTBP2, AR) in the same PCR reaction (N: normal DNA; T: tumor DNA; U: urine DNA).

The feasibility of this approach is shown in FIG. 4, where the three markers are multiplexed in a single PCR reaction. The results clearly demonstrate a novel band in urine DNA identical to the altered allele in the corresponding primary TCC tumor.

This assay is much simpler to perform that previous PCR-based assays followed by cloning and oligomer-specific hybridization to detect oncogene mutations (D. Sidransky, et al., supra). Although the sensitivity of this assay is slightly diminished, with cancer cell detection limited to a background of approximately 500 normal cells as compared to 10,000 normal cells using the previous approach, evidence from prior studies suggests that this is sufficient to detect cancer cells in most clinical specimens including sputum (FIG. 3). Moreover, rare oligoclonal events perhaps secondary to inflammation or hyperplasia would not be detected because of their dilution among an excess background of normal cells devoid of these alterations. Although oncogene mutations that provide neoplastic cells with a distinct growth advantage are not specifically detected, monoclonality is a fundamental characteristic of all neoplasms and detection of clonal cell populations in cytologic samples remains an ominous sign (P. J. Fialkow, Biochem. Biophys. Acta., 458:283, 1976; P. C. Nowell, Science, 94:23, 1976). The accumulation of genetic events in subsequent daughter cells is well recognized and a detectable clone would be expected to persist and probably continue along the neoplastic progression pathway (E. R. Fearon, et al., Cell, 61:709, 1990; D. Sidransky, et al., Nature, 355:846, 1992; D. Sidransky, et al., N. Engl. J. Med., 326:737, 1992).

Although many of the genetic events in colorectal cancer progression are known (E. R. Fearon, et al., supra), few events have been well-characterized in most other tumor types and not all occur in a given tumor. The ability to detect early clonal cell populations in patients without precise knowledge of the specific gene mutations in the primary tumor is a major strength of this assay. Indeed, these are precisely the patients that may be ideal candidates for chemopreventive strategies and/or amenable to surgical resection with careful follow-up. Moreover, detection of rare infiltrating cancer cells in histopathologic margins may have great impact on current surgical practice. Because the primary tumor is already resected in these cases, rapid screening of tumor DNA can provide a single marker for detection of these infiltrating tumor cells.

The present invention indicates that microsatellite alterations appear to be a common feature in human cancers and that larger repeats are probably more prone to this type of genetic instability. The high frequency of alterations observed in several markers appear to be tumor-type specific; the selection of appropriate markers with a relatively high rate of instability for a given tumor type may allow the use of a multiplex PCR test to identify a high percentage of neoplasms in patients. The identification of these alterations in bodily fluids and surgical margins attests to their potential use as clonal markers in the detection of neoplastic cells. A simple and powerful screening test applicable to a variety of cancers and pathologic samples is demonstrated by the present invention. Because cancer is so prevalent in the population, this molecular approach has important implications for cancer detection.

The invention now being fully described, it will be apparent to one of ordinary skill in the art that many changes and modifications can be made without departing from the spirit or scope of the invention.

I claim:

1. A method for detecting lung cancer in a sputum specimen, comprising the step of:
   testing a plurality of microsatellite markers in the specimen to determine a microsatellite marker length alteration relative to a control sample, wherein a microsatellite marker length alteration in the specimen relative to the control sample indicates the presence of a cancer in a lung which drains into the sputum.

2. A method for detecting cancer of an organ in a specimen of a body fluid which drains the organ, wherein the specimen is selected from the group consisting of: urine, sputum, bile, stool, cervical smears, tears, cerebral spinal fluid, and lymph nodes comprising the step of:
   testing a plurality of microsatellite markers in the specimen to determine a microsatellite marker length alteration relative to a control sample wherein a microsatellite marker length alteration in the specimen relative to the control sample indicates the presence of a cancer in the organ which drains into the body fluid.

3. A method for detecting bladder cancer in a urine specimen, comprising the step of:
   testing a plurality of microsatellite markers in the urine specimen to determine a microsatellite marker length alteration relative to a control sample, wherein a microsatellite marker length alteration in the urine specimen relative to the control sample indicates the presence of a cancer in an organ which drains into the urine.

4. The method of claim 1, 2, or 3 wherein the length alteration is an expansion of repeat units within the microsatellite marker.

5. The method of claim 1, 2, or 3 wherein the length alteration is a deletion of repeat units within the microsatellite marker.

6. The method of claim 1, 2, or 3 wherein the microsatellite marker comprises a tetranucleotide repeat.

7. The method of claim 1, 2, or 3 wherein the microsatellite marker comprises a trinucleotide repeat.

8. The method of claim 1, 2, or 3 further comprising the step of:

identifying the specimen as containing cancer cells.

9. The method of claim 1 wherein the lung cancer is Small Cell Lung Carcinoma.

10. The method of claim 1 wherein the lung cancer is Non-Small Cell Lung Carcinoma.

11. The method of claim 1 wherein the specimen is urine.

12. The method of claim 2 wherein the specimen is bile.

13. The method of claim 2 wherein the specimen is stool.

14. The method of claim 2 wherein the specimen is cervical smears.

15. The method of claim 2 wherein the specimen is tears.

16. The method of claim 2 wherein the specimen is cerebral spinal fluid.

17. The method of claim 2 wherein the specimen is lymph nodes.

* * * * *

UNITED STATES PATENT AND TRADEMARK OFFICE
CERTIFICATE OF CORRECTION

PATENT NO. : 6,479,234 B1  Page 1 of 1
APPLICATION NO. : 09/164764
DATED : November 12, 2002
INVENTOR(S) : David Sidransky It is certified that error appears in the above-identified patent and that said Letters Patent is hereby corrected as shown below:

Claim 11 at column 46, line 1 is replaced by the following:

11. The method of claim 3 wherein the cancer is Transitional Cell Carcinoma.

Signed and Sealed this

Twenty-third Day of September, 2008

JON W. DUDAS
*Director of the United States Patent and Trademark Office*